(12) United States Patent
Fink et al.

(10) Patent No.: US 9,056,294 B2
(45) Date of Patent: Jun. 16, 2015

(54) PARTICLE PUMP METHODS AND DEVICES

(75) Inventors: Jens Fink, Fredericia (DK); Niels Nielsen Poulsen, Vojens (DK)

(73) Assignee: Inbicon A/S, Fredericia (DK)

( * ) Notice: Subject to any disclaimer, the term of this patent is extended or adjusted under 35 U.S.C. 154(b) by 482 days.

(21) Appl. No.: 13/043,486

(22) Filed: Mar. 9, 2011

(65) Prior Publication Data

US 2011/0162741 A1 Jul. 7, 2011

Related U.S. Application Data

(62) Division of application No. 13/062,522, filed as application No. PCT/IB2010/053864 on Aug. 27, 2010.

(60) Provisional application No. 61/237,301, filed on Aug. 27, 2009, provisional application No. 61/318,431, filed on Mar. 29, 2010.

(51) Int. Cl.
*B65G 53/48* (2006.01)
*B01J 8/00* (2006.01)
(Continued)

(52) U.S. Cl.
CPC .............. *B01J 8/002* (2013.01); *B01J 8/0035* (2013.01); *B01J 2208/00752* (2013.01);
(Continued)

(58) Field of Classification Search
CPC ................ B01J 8/00; B01J 8/08; B01J 8/18; B01J 19/00; B01J 19/24; B01J 2208/00; B01J 2208/00743; B01J 2208/00752; B01J 2208/00769; B01J 8/0015; B01J 8/002; B01J 2208/00761; C10J 2200/00; C10J 2200/15; C10J 2200/156; B65G 51/00; B65G 51/04; B65G 51/08; B65G 51/10; B65G 51/14; B65G 53/00; B65G 53/34; B65G 53/40; B65G 53/48
USPC .............. 422/129, 232, 187; 137/561 R, 613; 141/37; 414/217, 800, 818
See application file for complete search history.

(56) References Cited

U.S. PATENT DOCUMENTS 1,481,088 A * 1/1924 Fujiyama ...................... 423/370
2,321,015 A 6/1943 Davis
(Continued)

FOREIGN PATENT DOCUMENTS

AU 2004243169 A1 12/2005
DE 3705275 A1 7/1988
(Continued)

OTHER PUBLICATIONS

Machine translation of claims and description of JP 2006-112341 A, which was published Apr. 27, 2006.*
(Continued)

*Primary Examiner* — Natasha Young
(74) *Attorney, Agent, or Firm* — Alston & Bird LLP

(57) ABSTRACT

Methods and devices are provided for transfer of particulate material, such as biomass feedstocks, into and out of pressurized reactors. Improved sluice devices have an L-shaped sluice chamber having an upper, vertical component in communication with a horizontal loading chamber and a lower component in communication with a vertical reactor inlet or outlet. Piston valves seal the sluice inlet and outlet by axial displacement across the vertical component of the sluice chamber and across the vertical reactor inlet or outlet. Relative to other methods for reactor unloading, these devices consume less steam and significantly reduce furfural content of unloaded, pretreated biomass. An optional hybrid plug/sluice method of biomass feeding using the devices permits biomass loading at sluice pressures intermediate between atmospheric and reactor pressure, thereby reducing "pump cycle" time and increasing biomass throughput capacity.

16 Claims, 5 Drawing Sheets

(51) Int. Cl.

| | | |
|---|---|---|
| B65G 53/00 | (2006.01) | |
| B65G 53/34 | (2006.01) | |
| B65G 53/40 | (2006.01) | |
| B65G 51/00 | (2006.01) | |
| B65G 51/04 | (2006.01) | |
| B65G 51/08 | (2006.01) | |
| B65G 51/10 | (2006.01) | |
| B65G 51/14 | (2006.01) | |
| B01J 8/08 | (2006.01) | |
| B01J 8/18 | (2006.01) | |
| B01J 19/00 | (2006.01) | |

(52) U.S. Cl.
CPC ............... B01J 2208/00761 (2013.01); B01J 2208/00769 (2013.01); Y02E 50/32 (2013.01); B65G 53/48 (2013.01); C12P 2201/00 (2013.01)

(56) References Cited

U.S. PATENT DOCUMENTS

| | | | |
|---|---|---|---|
| 3,042,229 A * | 7/1962 | Winter | 414/217 |
| 3,756,434 A | 9/1973 | Teske | |
| 3,776,150 A | 12/1973 | Evans et al. | |
| 3,841,465 A | 10/1974 | Miller, Jr. et al. | |
| 4,043,471 A * | 8/1977 | Trumbull et al. | 414/808 |
| 4,186,658 A | 2/1980 | Brown | |
| 4,274,786 A | 6/1981 | Svensson et al. | |
| 4,544,374 A | 10/1985 | Mallek et al. | |
| 4,912,237 A | 3/1990 | Zeitsch | |
| 4,922,650 A | 5/1990 | Akao et al. | |
| 5,095,825 A | 3/1992 | Arpalathi et al. | |
| 5,106,238 A | 4/1992 | Rehwinkel et al. | |
| 5,374,148 A * | 12/1994 | Kilpelainen et al. | 414/217 |
| 5,996,770 A | 12/1999 | Kjellqvist | |
| 6,506,282 B2 | 1/2003 | Hu et al. | |
| 7,314,538 B2 | 1/2008 | Lashofer et al. | |
| 7,380,554 B2 | 6/2008 | Ehling et al. | |
| 7,600,960 B2 | 10/2009 | Christensen et al. | |
| 7,850,904 B2 | 12/2010 | Osato et al. | |
| 7,976,259 B2 | 7/2011 | Craig et al. | |
| 8,328,947 B2 | 12/2012 | Anand et al. | |
| 2001/0020520 A1 | 9/2001 | Hu et al. | |
| 2006/0272557 A1 | 12/2006 | Liu et al. | |
| 2007/0084117 A1 * | 4/2007 | Van Den Born | 48/197 R |
| 2011/0000631 A1 | 1/2011 | Coles | |
| 2011/0162741 A1 | 7/2011 | Fink et al. | |
| 2011/0308141 A1 | 12/2011 | Christensen | |

FOREIGN PATENT DOCUMENTS

| | | |
|---|---|---|
| EP | 0044658 A1 | 1/1982 |
| EP | 0431639 A1 | 6/1991 |
| JP | S48-99873 A | 12/1973 |
| JP | S51-044107 B1 | 11/1976 |
| JP | 61-124440 A | 6/1986 |
| JP | 2006112341 A * | 4/2006 |
| SE | 456645 B | 10/1988 |
| SE | 500516 C2 | 7/1994 |
| WO | WO 93/00282 A1 | 1/1993 |
| WO | WO 93/10893 A1 | 6/1993 |
| WO | WO 03/013714 A1 | 2/2003 |
| WO | WO03013714 A3 | 2/2003 |
| WO | WO 03/050450 A1 | 6/2003 |
| WO | WO 2004/105927 A2 | 12/2004 |
| WO | WO2007009463 A2 | 1/2007 |
| WO | WO 2009/005441 A1 | 1/2009 |
| WO | WO 2009/147512 A2 | 12/2009 |

OTHER PUBLICATIONS

R. Curtis; H. Hatt: 'Equilibria in furfural-water systems under increased pressure and the influence of added salts upon the mutal solubilities of furfural and water' Australian Journal of Scientific Research Series A: Physical Sciences vol. 1, 1948, p. 213.

L. Hongquiang; C. Hongzhang: 'Detoxification of steam-exploded corn straw produced by an industrial-scale reactor' Process Biochemistry vol. 43, 2008, p. 1447.

International Searching Authority, International Search Report and Written Opinion for International Application No. PCT/IB2010/053864, Feb. 14, 2011, 13 pages, European Patent Office, The Netherlands.

The International Bureau of WIPO, International Preliminary Report on Patentability for International Application No. PCT/IB2010/053864, Feb. 28, 2012, 8 pages, Switzerland.

European Patent Office, Extended European Search Report for Application No. 12195019.0, Jan. 24, 2013, 5 pages, Germany.

* cited by examiner

PARTICLE PUMP METHODS AND DEVICES

This application is a divisional of co-pending application U.S. Ser. No. 13/062,522 filed Mar. 7, 2011 which is a national stage entry of PCT/IB2010/53864, now WO2011/024145, international filing date Aug. 27, 2010, which claims priority to U.S. 61/237,301, filed Aug. 27, 2009, and to U.S. 61/318,431, filed 29 Mar. 2010.

FIELD OF THE INVENTION

The invention relates in general to devices and methods for transfer of particulate material into and out of pressurized reactors and in particular to devices and methods for feeding biomass feedstocks into and out of pressurized hydrothermal reactors.

BACKGROUND

Commercial production of bioethanol and other useful products from lignocellulosic biomass requires high levels of feedstock throughput, on the order of 10 to 50 metric tons dry matter per hour. In biomass conversion systems that rely upon hydrothermal pretreatment of feedstocks prior to enzymatic hydrolysis, the scale of processing can be limited by the rate at which particulate material can be fed into pressurized pretreatment reactors.

Systems for "feeding" biomass into pressurized reactors generally fall into one of two predominant categories—plug feeders and sluice feeders. Plug feeders are well known in the pulp and paper industry. These use loading devices such as screws, pistons, and combination piston-screws to compact particulate material to a sufficient effective density so as to form a gas impenetrable pressure seal or "plug." This plug is then continuously formed and loaded into a reactor against high pressures. Plug feeders have been reported to efficiently load against pressures from 4 to 10 bar. A variety of different plug feeder schemes have been reported. Some screw-plug feeders rely on a very long feeding screw, which permits loading at somewhat lower effective biomass plug density. Systems relying on higher effective density often utilize a disintegrator device on the pressurized reactor side to break apart the high density plug. See for example U.S. Pat. No. 3,841,465; U.S. Pat. No. 4,186,658; U.S. Pat. No. 4,274,786; U.S. Pat. No. 5,996,770; WO2003/050450; WO2004/105927; WO2009/005441.

Sluice feeders rely on a system of pressure locks, at least one of which is kept closed at all times. Particulate material is loaded into a sluice chamber through an open inlet valve. The inlet valve is then closed and the material unloaded into a high pressure reactor through an open outlet valve. A variety of sluice feeder systems have also been reported. See for example U.S. Pat. No. 5,095,825; SE 456,645; SE 500,516; WO1993/010893; WO1993/000282; WO2003/013714.

Individual sluice feeders generally have a lower capacity but provide a higher level of operational safety relative to plug feeders. Biomass is invariably heterogeneous material. Thus, even a highly compressed plug can contain channels through which potentially explosive release of pressurized steam may occur. In providing a mechanical valve seal against reactor pressure at all times, sluice feeders greatly reduce the risk of explosive release.

High density plug feeders have generally been considered advantageous over sluice feeders in that they can be readily scaled to very large capacity. However, plug feeders also have several notable disadvantages. Plug feeders have not been shown to operate effectively at pressures >10 bar. They are typically operated at very high levels of feedstock compression, in part to minimize occupational hazards. Biomass is typically pressurized to levels much higher than nominally required to seal against reactor pressure. As a consequence, plug feeders generate tremendous frictional forces between the plug and the feeding apparatus. This reduces energy efficiency and also introduces high levels of mechanical wear-and-tear, particularly with feedstocks having high sand or silica content such as wheat straw, rice straw and corn stover. Refurbishing of the "plug screw" or other loading device in plug feeders is routine maintenance which may be required on intervals as brief as 1-3 months. This introduces production inefficiencies as well as high maintenance costs. Plug feeders also typically require that feedstocks be subject to particle size reduction and extensive washing, which introduces additional process steps as well as increased energy requirements and running costs.

These disadvantages of plug feeders have been successfully avoided on a pilot production scale of 1 metric ton dry matter per hour using the single sluice chamber feeder system described in WO2003/013714, which is hereby incorporated by reference in entirety. Using this system, biomass can be efficiently loaded against pressures >15 bar. Feedstocks are processed without extensive particle size reduction or washing, first portioned into pre-determined portions, then force-loaded into a horizontal sluice chamber by means of a piston screw or similar device, the axis of which is practically in line with the axis of the sluice chamber.

We have discovered a variety of means whereby this sluice system can be scaled to larger capacity with increased operational safety and efficiency.

Further, we have discovered that sluice systems provide improved means for removing pretreated biomass from pressurized reactors. Plug feeders do not, themselves, provide means for removing pretreated biomass. Previously, pretreated biomass has typically been removed using "steam explosion" systems or "hydrocyclone" systems such as those described in WO 2009/147512, which is hereby incorporated by reference in entirety. Hydrocyclone systems were previously viewed as advantageous due to relatively conservative steam losses associated with removal of pretreated biomass. By using particle pump outlets to remove pretreated biomass, significant improvements over the performance of steam explosion and hydrocyclone systems can be obtained. In particular, relative to hydrocyclone systems, concentrations of the fermentation inhibitor furfural in the pretreated biomass released from the reactor can be reduced by more than 50%. Relative to steam explosion systems, both furfural content in released pretreated biomass and also steam losses associated with removal of pretreated biomass can be reduced.

These and other improvements are described in detail herein.

SUMMARY

Methods and devices are provided for transfer of particulate material, such as biomass feedstocks, into and out of pressurized reactors. Improved sluice devices have an L-shaped sluice chamber having an upper, vertical component in communication with a horizontal loading chamber and a lower component in communication with a vertical reactor inlet or outlet. Piston valves seal the sluice inlet and outlet by axial displacement across the vertical component of the sluice chamber and across the vertical reactor inlet or outlet. Relative to other methods for reactor unloading, these devices consume less steam and significantly reduce furfural content of unloaded, pretreated biomass. An optional hybrid plug/sluice method of biomass feeding using the devices permits biomass loading at sluice pressures intermediate between atmospheric and reactor pressure, thereby reducing "pump cycle" time and increasing biomass throughput capacity.

DETAILED DESCRIPTION OF PREFERRED EMBODIMENTS

Figure 1:
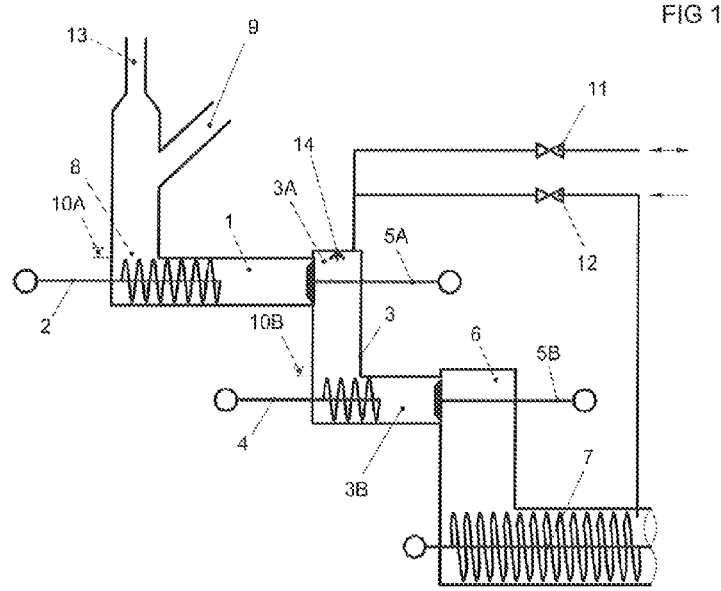
FIG. 1 shows a schematic illustration of a preferred embodiment.

The single sluice chamber feeder system of WO2003/013714 provides a horizontal sluice chamber in which the piston screw unloading device is practically in-line with the axis of the sluice chamber. Using this system, guillotine-type valves are generally preferred as pressure locks for the sluice inlet and outlet.

We have discovered that piston valves can be used at the sluice inlet by aligning the axis of the loading device at an angle to the axis of the sluice chamber, preferably perpendicular. Piston valves are advantageous in that these are less prone to clogging and mechanical wear and are more readily scalable to large sizes than guillotine-type valves.

The axis of the loading device can be aligned at an angle to the axis of the sluice chamber by use of a vertical sluice chamber through which biomass falls by force of gravity. The risk of "bridging" is increased within a vertical sluice chamber, particularly using non-flowing or comparatively high dry matter feedstocks which have not been subject to extensive particle size reduction. Accordingly, vertical sluice chambers were previously considered undesirable for sluice feeding biomass feedstocks. We have discovered that "bridging" can be effectively avoided through use of an L-shaped sluice chamber. This has both an upper, vertical component and, also, a lower unloading segment through which an unloading device adapted for force-unloading is axially displaceable. By aligning the axis of the unloading device at an angle to the axis of the reactor inlet, preferably perpendicular, it is also possible to use piston valves as pressure locks for the sluice outlet.

The introduction of a sluice chamber having a horizontal unloading segment fitted with an additional device for force-unloading provides surprising resistance to sudden pressure change. This increases operational safety and ensures that a safety chimney, which dissipates sudden pressure release from the sluice chamber, need only be constructed to tolerate minor pressure changes.

The use of both loading and unloading devices aligned at an angle, preferably perpendicular, with the sluice chamber and reactor inlet respectively permits a hybrid plug/sluice method of biomass feeding. In some embodiments, compression of biomass by the loading device within the loading chamber and compression of biomass by the unloading device within the unloading segment of the sluice chamber creates comparatively low-density plugs. These plugs can effectively seal against pressures intermediate between atmospheric and reactor pressure. Plug partial sealing permits a hybrid plug/sluice mode of operation in which biomass may be loaded without fully equilibrating pressure within the sluice chamber to atmospheric pressure and in which biomass may be unloaded without fully equilibrating pressure within the sluice chamber to reactor pressure. This hybrid operation mode reduces "pump cycle" time of the sluice device and accordingly increases its throughput capacity. Cycle time can be further decreased by introducing cool water mist into the sluice chamber during depressurization.

Surprisingly, significant operational advantages can also be obtained using a sluice chamber feeding device, or "particle pump," to not feed but remove pretreated biomass from pressurized hydrothermal reactors. Most notably, concentrations of the fermentation inhibitor furfural, produced as a byproduct of hydrothermal pretreatment, that remain in pretreated biomass after unloading are significantly reduced. Where equivalent biomass is pretreated under equivalent conditions but removed using a sluice system compared with a hydrocyclone system, furfural levels obtained in the insoluble fiber fraction are typically reduced by at least 50%. As is well known in the art, concentrations of furfural produced as a byproduct of hydrothermal pretreatment raises a significant obstacle to effective second generation fermentation processes such that detoxification process steps are typically required.

Without wishing to be bound by theory, it is believed that this surprising advantage of a particle pump outlet is due to subtleties of the furfural/water phase equilibrium within a pressurized hydrothermal reactor. At the relatively dilute concentrations of furfural typically achieved in hydrothermal pretreatment, mol %<0.5 at 35% dry matter, and in the high temperature and pressure regime of a hydrothermal pretreatment reactor, typically between about 160 to 230° C. and between about 10 to 20 bar pressure, furfural is expected to exist primarily in the vapour phase, relative to liquid phase, by a factor of at least about 4:1. (See e.g. R. Curtis and H. Hatt, "Equilibria in furfural-water systems under increased pressure and the influence of added salts upon the mutual solubilities of furfural and water," Australian Journal of Scientific Research Series A: Physical Sciences (1948) 1:213.) During the removal cycle, using a particle pump outlet, equilibration of the outlet sluice chamber to low pressure is associated with venting of vapour phase from the pretreated biomass under controlled conditions, prior to removal, effectively stripping the great bulk of furfural content.

Two experimental pretreatment reactors in our laboratories in Skærbæk, Denmark, having respective throughput capacities of 100 and 1000 kg/hour biomass, were alternatively fitted with hydrocyclone biomass outlets (1000 kg/hr), as described in WO 2009/147512, or with a simple single-chamber horizontal sluice chamber outlet (100 kg/hr), similar to the single-chamber sluice feeder system described in WO2003/013714. Both systems were used to pretreat wheat straw under equivalent conditions, to severity about 3.88, at 14 bar pressure, 190° C. Pretreated wheat straw unloaded using both systems was pressed into a fiber and liquid fraction. The pressed fiber fractions were subsequently washed using the same belt press washing apparatus, operated in equivalent conditions.

Washed fiber fractions from pretreated wheat straw unloaded using the particle pump outlet were sampled on 3 separate dates, after the pretreatment system was operating at steady-state. Washed fiber fractions from pretreated wheat straw unloaded using the hydrocylone outlet were sampled on 6 separate dates after the pretreatment system was operating at steady-state. The particle-pump unloaded biomass had significantly lower furfural levels, 0.79+/−0.04 g/kg, compared with hydrocyclone unloaded biomass, 1.65+/−0.24 g/kg, t,p<0.005. While direct measurements of furfural content in the initial pressed fiber fraction from the hydrocyclone unloaded biomass were not made, these values can be readily extrapolated from the direct washed fiber values by applying an averaged pressed/washed furfural ratio obtained using this system. Furfural content in pressed fiber fractions obtained using the particle pump outlet was significantly lower than furfural content of the calculated pressed fiber fraction obtained using the hydrocyclone outlet, 1.59+/−0.14 g/kg compared with 4.61+/−0.58 g/kg, t, p<0.003.

The particle pump outlet provides significant reduction in furfural content of the insoluble fiber fraction obtained from pretreated biomass, at least 50%, apparently as a simple effect of controlled steam venting during the unloading (depressurization) cycle. It will be readily understood by those skilled in the art that particle pump outlets may be optimized to achieve even greater reductions of furfural content. The simple single-chamber, horizontal sluice chamber system used in the experiments reported here could achieve at least 50% reductions in furfural content, where depressurization from 14 bar to 2 bar was conducted in a cycle of about 1 minute, and where temperature was reduced from 190° C. to about 100° C. Biomass was ejected at about 2 bar, at about 100° C. Much deeper reductions in furfural content could be achieved by simply ejecting the biomass at 2 bar into an outlet chamber, in which pressure was further reduced to sub-atmospheric levels, preferably between 50 and 200 torr, and preferably at temperatures above 140° C. as described in U.S. Pat. No. 4,912,237, which is hereby incorporated by reference in entirety. Through routine experimentation, one skilled in the art can readily optimize biomass ejection using a particle pump outlet to conditions that achieve optimal furfural reduction.

Particle pump methods of removing pretreated biomass are, in any case, advantageous relative to steam explosion methods in that steam consumption is reduced. "Cooking steam" consumption with our hydrothermal reactor fitted with a particle pump outlet averaged approximately 160 kg/steam per 1000 kg biomass feedstock pretreated. In contrast, similar reactors operated at similar pretreatment severities but fitted with steam explosion outlets typically report higher "cooking steam" consumption, on the order of 250-350 kg/steam per 1000 kg biomass feedstock pretreated.

Particle pump outlets are also advantageous relative to steam explosion in terms of reduction of furfural content in pretreated biomass removed from the reactor. Again without wishing to be bound by theory, it is believed that pretreated biomass removed from the reactor through particle pump outlets have lowered furfural content relative to material removed through steam explosion outlets also due to subtleties of the furfural/water phase equilibrium. In steam explosion, pretreated biomass is suddenly released from high pressure reactor conditions, which favour liquid phase of water and which favour vapour phase of furfural at the low concentrations of furfural typically experienced. At atmospheric pressure, vapour phase of water in the hot biomass is favoured, resulting in an explosive vaporization of water within the hot biomass that disrupts cellulose chains, contributing to a beneficial overall pretreatment effect. However, as the steam-exploded biomass cools to temperatures below 100° C., or at least below 97.9° C., furfural is expected to condense into the biomass. See e.g. G. H. Mains, Chem. Met. Eng. (1922) 26:779. Accordingly, much higher furfural levels are reported in steam-exploded biomass treated at similar severities and unloaded at similar pressures than the furfural levels reported here in pretreated biomass unloaded through a particle pump outlet. See e.g. L. Hongquiang and C. Hongzhang, "Detoxification of steam-exploded corn straw produced by an industrial-scale reactor," *Process Biochemistry* (2008) 43:1447.

In some embodiments, the invention provides an apparatus for transfer of particulate matter into or out of a pressurized reactor comprising:

(a). A loading chamber,
(b). A loading device situated within the loading chamber,
(c). An L-shaped sluice chamber having an upper vertical component in communication with the loading chamber and having a lower component in communication with a vertical reactor inlet or outlet,
(d). A sluice inlet piston valve which is axially displaceable across the vertical component of the sluice chamber and which is adapted to seal the opening from the loading chamber into the vertical component of the sluice chamber,
(e). An unloading device which is axially displaceable within the lower component of the sluice chamber, and
(f). A sluice outlet piston valve which is axially displaceable across the vertical reactor inlet or outlet and which is adapted to seal the opening from the lower component of the sluice chamber into the reactor inlet or outlet.

The loading chamber has at least one opening through which biomass feedstocks may be introduced and is aligned in communication with (i.e., having an opening to) the vertical component of an L-shaped sluice chamber. In some embodiments, the loading chamber provides a containment in which biomass feedstock can be compressed, portioned or otherwise conditioned prior to force-loading into the sluice chamber. In preferred embodiments, the loading chamber is approximately horizontal and communication with the vertical component of the sluice chamber is approximately perpendicular. In other embodiments, the loading chamber may be upwardly or downwardly sloping, aligning with the vertical component of the sluice chamber at an angle between about 70-120 degrees. In some embodiments, the loading chamber is equipped with an axially displaceable loading device that compresses biomass feedstock while the sluice inlet valve is closed and that force-loads compressed biomass into the sluice chamber. In other embodiments, the loading chamber may simply be a container within which a loading device operates to force-load biomass into the sluice chamber.

A suitable loading device may comprise a screw conveyor, a piston-screw, or a piston. In some embodiments, it is advantageous to compress biomass feedstocks during loading. Thus in some embodiments the loading device is able to provide compression of biomass feedstocks to within the range of about 200-400 kg/m$^3$. In preferred embodiments, the loading device is a piston screw. Also in preferred embodiments, the device is rotable in either clockwise or counter-clockwise orientations. Mechanical resistance to the motor which rotates the piston screw can readily be calibrated to provide an accurate measurement of biomass compaction. In some embodiments, biomass loading of the loading chamber is typically conducted by first compressing biomass against a closed sluice inlet valve, then loading the compressed biomass into the sluice chamber by axial displacement of the loading device. In other embodiments, where compression of biomass during loading is not desired, the loading device force-loads biomass directly into the sluice chamber through an open sluice inlet valve, achieving little compression of the biomass. In some embodiments, especially where compression of biomass is desired, the loading device is axially displaceable within the loading chamber. In other embodiments, especially where compression of biomass is not desired, the loading device may be fixed within a relatively small loading chamber that effectively provides little more than a container within which biomass is collected and force-loaded by the loading device.

The sluice chamber is L-shaped. As used herein, the term "L-shaped" refers to a device having both an upper, vertical component and a lower component. The term "vertical" as used herein means aligned with the direction of the force of gravity, +/−10%. In preferred embodiments, the lower component is approximately horizontal and communication between the upper and lower components is approximately perpendicular. In other embodiments, the lower component may be upwardly or downwardly sloping, aligning with the vertical component of the sluice chamber at an angle between about 70-120 degrees. In preferred embodiments, the vertical component of the sluice chamber has an internal diameter larger than the internal diameter of the loading chamber, so as to further reduce the risk of biomass bridging. Although the term "L-shaped" is used, one skilled in the art will readily understand that either the vertical or the lower component may be longer than the other, or both may be of equivalent length.

In some embodiments, the sluice chamber can be equipped with means for injecting cool water mist. In general, pressurization to reactor pressure is comparatively faster than depressurization to loading pressure. It is thus advantageous to enhance the rate of sluice chamber depressurization, since this in turn reduces cycle time of sluice chamber loading, pressurization, unloading, and depressurization. Cool water mist is believed to enhance the rate of depressurization by facilitating condensation of pressurized steam.

The lower component of the sluice chamber, or unloading segment, is aligned in communication with a vertical reactor inlet or outlet. In preferred embodiments, the unloading segment is approximately horizontal and communication with the vertical reactor inlet or outlet is approximately perpendicular. The unloading segment is equipped with an axially displaceable unloading device that, optionally, compresses biomass feedstock while the sluice outlet valve is closed and that force-unloads biomass into the vertical reactor inlet or out of the reactor outlet. Alternatively, the unloading device may force-unload biomass directly through an open sluice outlet valve, without achieving compression of biomass during unloading.

Similar to the loading device, a suitable unloading device may comprise a screw conveyor, a piston-screw, or a piston and, in preferred embodiments, is rotable in either clockwise or counter-clockwise orientations.

The angular connections between the loading chamber and the upper, vertical component of the sluice chamber and between the lower component of the sluice chamber and the vertical reactor inlet or outlet permit use of piston valves as pressure locks. Piston valves are comparatively less prone to clogging and mechanical wear and are more readily scalable to large sizes than other valve systems such as guillotine type valves, which are preferred, where the axis of the loading device is in-line with the axis of the sluice chamber. The piston valves are axially displaceable across the vertical component of the sluice chamber and across the vertical reactor inlet or outlet and are adapted to seal the sluice inlet and outlet.

In preferred embodiments, both the sluice inlet and the sluice outlet piston valves comprise a rotating disc. Rotation of the disc-shaped valve during closure clears the sluice inlet and outlet valve seat of biomass, which can otherwise accumulate. In preferred embodiments, the sluice inlet and outlet piston valves displace substantially in line with the displacement of the loading and unloading devices respectively. In some embodiments, the sluice inlet and/or sluice outlet valve may be fitted with blades or other means for disintegrating compressed biomass. Disintegration means helps avoid entry into the reactor of compressed biomass "clumps," which can interfere with even heating of biomass and result in suboptimal pretreatment.

In some embodiments, the loading device, unloading device and piston valves may be actuated by hydraulic cylinders. These are reliable and readily scalable to large sizes. However, these require approved valves and control programs as well as regular inspection of the mechanical components. Accordingly, in some embodiments electrical driven actuators may be used, which generally have improved energy efficiency as well as a simpler and more cost optimal design. The electrical-powered actuators are also self-locking, in that these can only actuate if the motor is powered, resulting in improved safety relative to hydraulic cylinders.

In some embodiments, the vertical reactor inlet may comprise disintegrator means or other means for facilitating even heating of loaded biomass within the reactor.

FIG. 1 provides a schematic illustration of one preferred embodiment that is able to optionally operate in hybrid plug/sluice mode of biomass feeding. The device has a horizontal loading chamber (1) equipped with a loading device, piston screw (2), that is rotable and axially displaceable within the loading chamber (1). An L-shaped sluice chamber (3) is provided that has both an upper, vertical component (3a), in perpendicular communication with the loading chamber (1), and also a lower, horizontal component or unloading segment (3b) equipped with an unloading device, piston screw (4), that is rotable and axially displaceable within the unloading segment (3b). The loading chamber can be opened or sealed by a sluice inlet piston valve (5a), which is axially displaceable across the vertical component of the sluice chamber, which is adapted to seal the opening from the loading chamber to the sluice chamber, and which opens and closes in line with the displacement of the loading piston screw. The unloading segment (3b) of the sluice chamber is in perpendicular communication with a vertical reactor inlet (6). The unloading segment can be opened or sealed by a sluice outlet piston valve (5b), which is axially displaceable across the vertical reactor inlet (6), which is adapted to seal the opening from the lower, horizontal component of the sluice chamber to the reactor inlet, and which opens and closes in line with the displacement of the unloading piston screw. The reactor is equipped with a feeding screw (7) that carries loaded feedstock through the reactor to an outlet from which pretreated material emerges. Biomass feedstock is pre-portioned into pre-defined quantities and fed to the loading chamber through at least one opening (8) via a chute or hopper (9). The preferred particle pump embodiment shown is further equipped with a biomass level sensor (10a), that detects the level of accumulated feedstock material awaiting force-loading into the loading chamber (1), and a level sensor (10b) that detects the level of accumulated feedstock material awaiting force-unloading through the unloading segment (3b). The device is further equipped with a valve (11) which, during pressure adjustment, releases pressurized steam from the sluice chamber to process solution recycling or introduces fresh steam, and valve (12) that introduce pressurized reactor steam into the sluice chamber during pressure adjustment. The device is further equipped with a safety chimney (13) and a cool water mist injector (14) that injects cool mist into the sluice chamber to accelerate depressurization to loading pressure.

Figure 2:
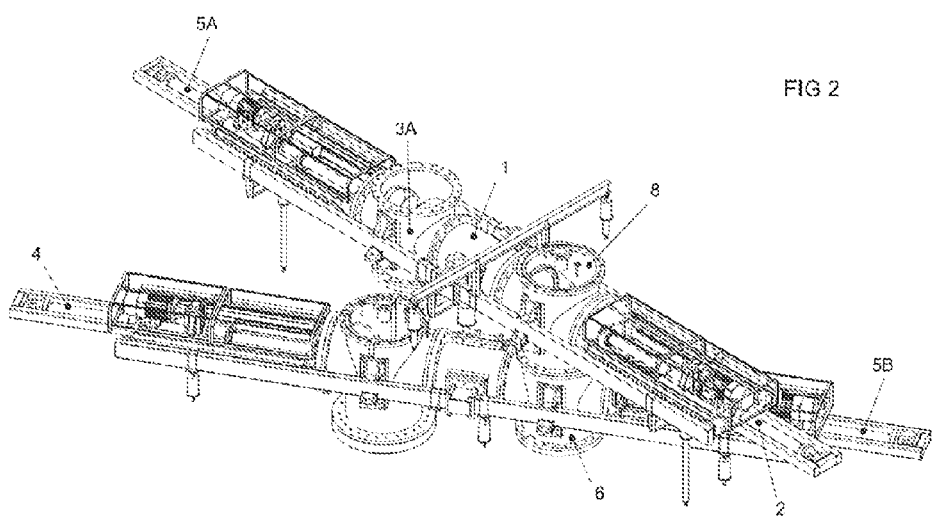
FIG. 2 shows a side-angle view of a preferred embodiment actuated by hydraulic cylinders.

FIG. 2 provides a side-angle view of a preferred embodiment of the device. In this view, the loading chamber (1), an opening to the loading chamber through which biomass is fed (8), the loading device (2), and the inlet piston valve (5a) can be discerned in the upper portion of the device. The unloading device (4), the outlet piston valve (5b) and the reactor inlet (6) can be discerned in the lower portion of the device. The upper and lower portions of the device as shown are arranged in an arbitrary orientation. The upper and lower portions can alternatively be arranged parallel or at any angle that suits space limitations or other requirements.

Figure 3:
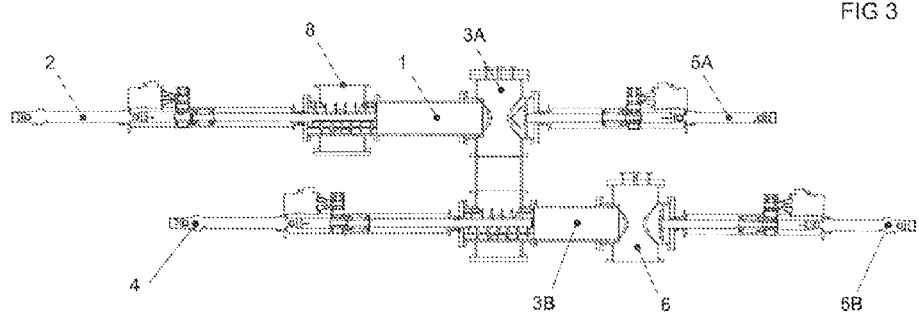
FIG. 3 shows a section-view of the preferred embodiment shown in FIG. 2.

FIG. 3 provides a section-view of the embodiment shown in FIG. 2. This embodiment is adapted to sustain throughput of at least 4 metric tons dry matter per hour into a reactor pressurized to 15 bar. The loading chamber (1) is cylindrical, about 2 meters in length, having an internal diameter of about 0.7 meters, and fitted with grooves that guide displacement of the loading piston-screw. The loading piston-screw (2) comprises a screw component about 0.7 meters in length, and is adapted to displace axially within the loading chamber. The unloading segment (3b) of the L-shaped sluice chamber is similarly cylindrical, having an internal diameter of about 0.7 meters. The vertical component (3a) of the L-shaped sluice chamber is similarly cylindrical but has larger internal diameter, about 1 meter. The biomass opening (8), sluice inlet piston valve (5a), unloading piston screw (4), reactor inlet (6), and sluice outlet piston valve (5b) are also shown.

Figure 4:
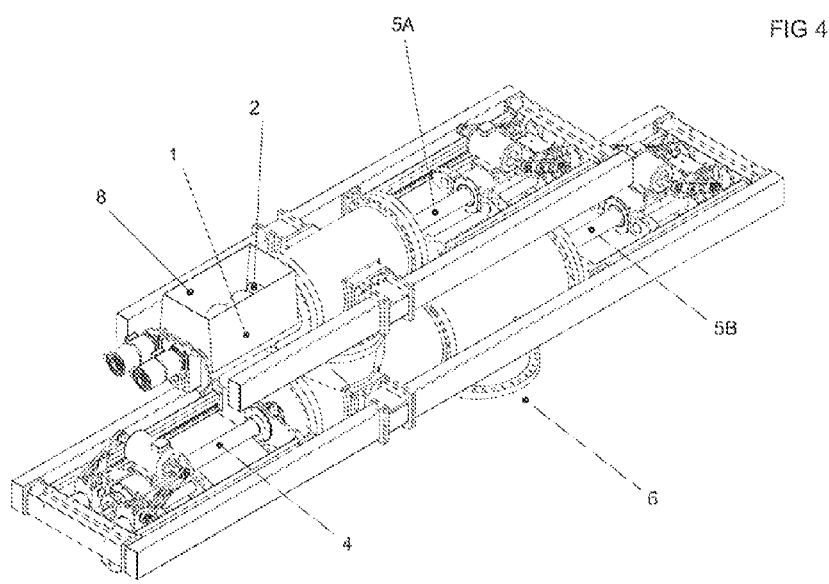
FIG. 4 shows a side-angle view of a preferred embodiment actuated by electrical drives.

FIG. 4 provides a side-angle view of one alternative embodiment that is generally not adapted for hybrid plug/sluice mode of biomass feeding. In this embodiment, the loading chamber (1) is essentially simply a container with an opening (8) to a biomass feed chute within which container the loading device (2) operates. The loading device (2), sluice inlet piston valve (5A), the unloading piston screw (4) and the sluice outlet piston valve (5B) are driven by electrical-powered actuators.

Figure 5:
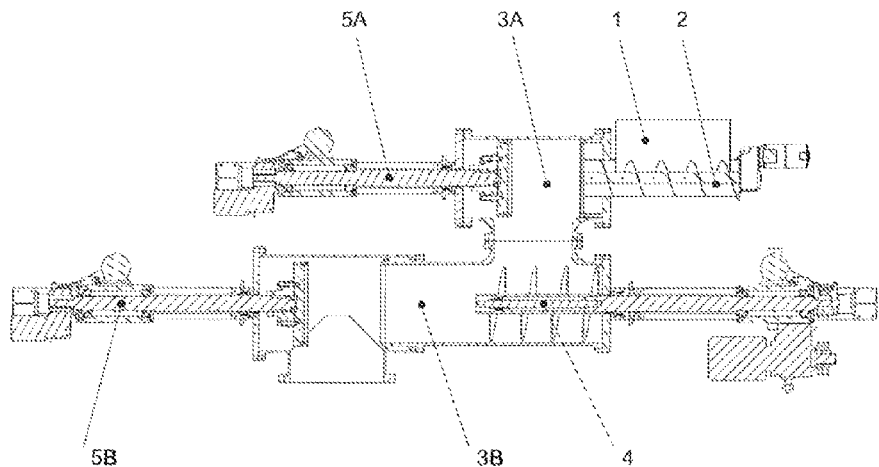
FIG. 5 shows a section-view of the embodiment shown in FIG. 4.

FIG. 5 provides a section-view of the embodiment shown in FIG. 4. This embodiment is adapted to sustain throughput of at least 10 metric tons dry matter per hour into a reactor pressurized to 15 bar. The loading chamber (1) provides little more than a containment for the loading device (2). The loading device (2) comprises two fixed screw conveyors, diameter about 0.45 m, that provide little compression of the biomass during loading. The vertical component of the sluice chamber (3A) is about 1.8 m in length, shorter than the unloading segment of the sluice chamber (3B) which is about 2.8 m in length. Both components of the sluice chamber have diameter about 1.0 m. In preferred modes of operation where biomass is fed into a pressurized reactor, the device loads biomass without appreciable compression through an open sluice inlet valve. The sluice inlet valve is closed, and sluice chamber pressure equalized to approximately reactor pressure. The sluice outlet valve is then opened and biomass force unloaded by screw action and axial displacement of the unloading device (2).

In some embodiments, the invention provides an apparatus for removing pretreated biomass from a pressurized hydrothermal reactor comprising A sluice chamber loading device
A sluice chamber
A sluice chamber inlet valve adapted to seal an opening to reactor pressure when closed A sluice chamber outlet valve adapted to seal an opening to atmospheric or outlet pressure when closed and adapted for non-explosive release of pretreated biomass
A sluice chamber unloading device, and
A biomass outlet adapted for non-explosive release of pretreated biomass.

A sluice chamber as used herein is a chamber which alternately can be opened to one of two pressure zones, while maintaining a pressure tight separation from the other pressure zone. Non-explosive release refers to release in such manner that biomass is substantially depressurized relative to reactor pressure before release. Atmospheric pressure as used herein includes levels up to about 0.3 bar above atmospheric pressure. Outlet pressure refers to a pressure lower than reactor pressure, but somewhat above or below atmospheric pressure at which pretreated biomass is removed from a pressurized reactor. The sluice chamber outlet valve can be adapted for non-explosive release of pretreated biomass by having a cross-sectional area approximately the same or greater than the cross-sectional area of the sluice chamber. Biomass outlet refers to a channel or chamber or combination of channels, conveyances and chambers through which pretreated biomass is removed from the pressurized reactor. The biomass outlet can be adapted for non-explosive release by having an opening to the sluice chamber outlet valve that has an aperture of approximately the same or greater cross-sectional area as the valve itself. In some embodiments, the removal device may be fitted with an outlet chamber that is adapted to provide variable temperature and pressure conditions. By controlling pressure conditions in the outlet chamber, pretreated biomass removed from a pressurized reactor can be subject to physical chemical manipulations aimed at further reducing the content of fermentation inhibitors or other components in the pretreated biomass prior to further processing. For example, in some embodiments, the removal device may be fitted with an outlet chamber that provides sub-atmospheric pressures, preferably within the range of about 50 to 200 torr, at a temperature of above about 140° C. to further strip furfural from pretreated biomass prior to further processing.

In preferred embodiments, the device is adapted to vent steam during depressurization of the sluice chamber in such manner that pretreated biomass within the sluice chamber experiences an environment having substantially lowered furfural content prior to removal from the reactor.

The device is preferably fitted with ventilation valves that can be regulated so as to release reactor steam and thereby depressurize the sluice chamber in a process that is comparatively gradual relative to steam explosion. In preferred embodiments, the device can be fitted with separate ventilation valve systems that ventilate steam from reactor pressures, typically 10-20 bar, down to intermediate levels of pressures, for example 3 bar, and from intermediate levels of pressure down to outlet pressures. It will be readily understood that the separate ventilations systems may comprise two, three, four or more stages, for example, from 15 to 10 bar, from 10 to 8, from 8 to 5, from 5 to 3, and from 3 to 1. Steam ventilated in each of the separate systems can then be recycled to different production processes such as drying systems, evaporation systems, biomass preheating and other processes. In one preferred embodiment, the device has two ventilation valve systems, one that ventilates from 15 bar to 3 bar and a second that ventilates from 3 bar to atmospheric.

Any of the embodiments of the transfer apparatus described here could provide suitable removal devices by appropriate adaptation and orientation of the sluice chamber and the sluice chamber inlet and outlet valves and by adaptation of the reactor outlet for non-explosive release of pretreated biomass. Suitable loading and unloading devices are as described previously. The sluice chamber need not be limited to L-shaped embodiments but may be arranged in any suitable configuration. The sluice chamber inlet and outlet piston valves need not be limited to piston valves but may be arranged in any suitable configuration. Any of the embodiments of the sluice devices described in WO 2003/013714 could provide suitable removal devices by appropriate adaptation and orientation of the sluice chamber and the sluice chamber inlet and outlet valves and by introduction of a biomass outlet adapted for non-explosive release of pretreated biomass.

Figure 6:
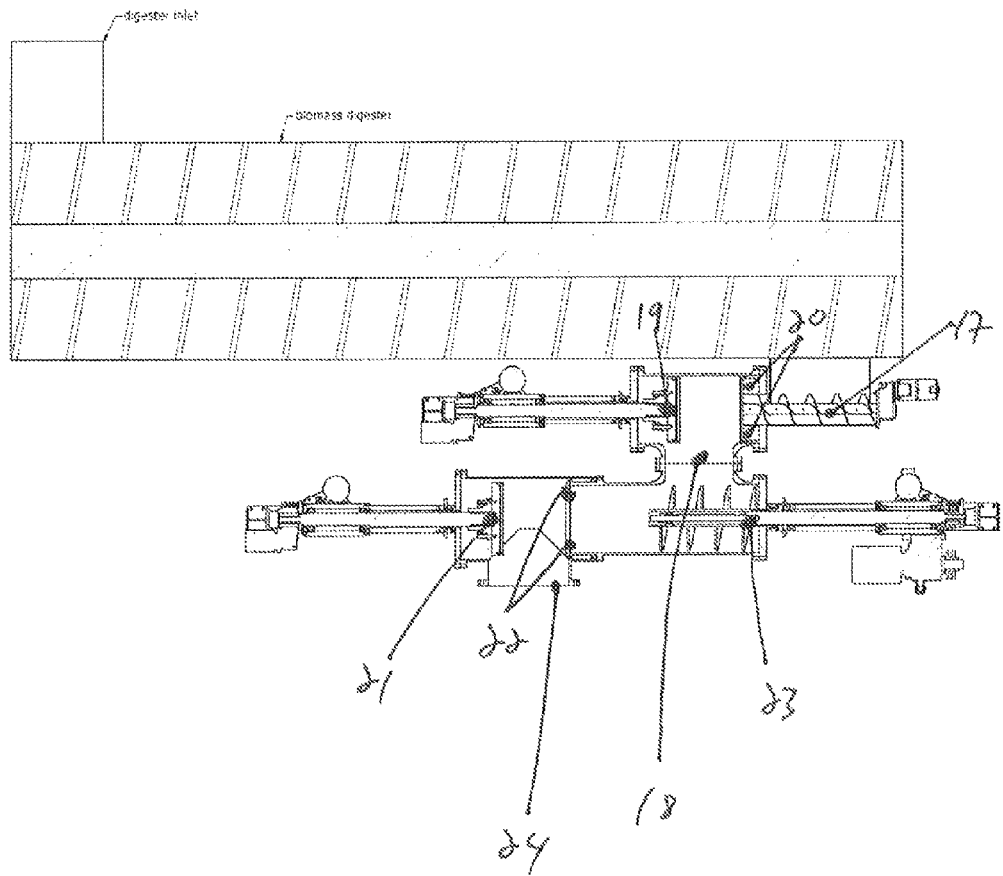
FIG. 6 shows adaptation of a preferred embodiment for removal of pretreated biomass from a pressurized reactor.

FIG. 6 shows adaptation of the embodiment shown in FIG. 5 for use as a removal device according to the invention. Shown are sluice chamber loading device (17), sluice chamber (18),
sluice chamber inlet valve (19), opening to reactor pressure (20), sluice chamber outlet valve (21), opening to atmospheric or outlet pressure (22), sluice chamber unloading device (23), and
biomass outlet adapted for non-explosive release of pretreated biomass (24).

In some embodiments, the invention provides a method for removing pretreated biomass from pressurized hydrothermal reactors, comprising Loading pretreated biomass from a pressurized reactor into a sluice chamber through an open inlet valve that is adapted to seal an opening to reactor pressure when closed, at a time when the outlet valve is closed, which outlet valve is adapted to seal an opening to atmospheric or outlet pressure when closed is Closing the inlet valve, Depressurizing the sluice chamber from reactor pressure to atmospheric or outlet pressure Opening the outlet valve, Unloading the pretreated biomass at atmospheric or outlet pressure, Closing the outlet valve, and Repressurizing the sluice chamber to reactor pressure prior to opening the inlet valve for an additional removal cycle.

Preferred embodiments are characterized by depressurization of the sluice chamber in such manner that pretreated biomass within the sluice chamber experiences an environment having substantially lowered furfural content prior to removal from the reactor. In preferred embodiments, furfural content of the insoluble fiber content of unloaded biomass is less than 50% of furfural content within the reactor. In some embodiments, depressurization is accomplished by means of separate ventilation valve systems that ventilate steam from reactor pressures, typically 10-20 bar, down to intermediate levels of pressures, for example 3 bar, and from intermediate levels of pressure down to outlet pressures. In one preferred embodiment, depressurization is accomplished using two ventilation valve systems, one that ventilates from 15 bar to 3 bar and a second that ventilates from 3 bar to atmospheric. In preferred embodiments, steam ventilated during depressurization is recycled to use in further production processes such as drying systems, evaporation systems, or biomass preheating. In some embodiments, the process is further characterized by subjecting the unloaded biomass to further adjustments of pressure and temperature in a biomass outlet chamber. In preferred embodiments, the unloaded biomass is subject to conditions of pressure between about 50 torr and 200 torr, or between about 200 torr and 700 torr, and temperatures of at least 140° C. In preferred embodiments, pressure within the sluice chamber is depressurized from about 15 bar to about 0.3 bar over a period of about 40 seconds.

In some embodiments, the invention provides a method for loading biomass feedstock into a pressurized reactor comprising:

(a). force-loading biomass into a loading chamber that is in communication with the upper, vertical segment of an L-shaped sluice chamber, achieving compression of biomass while the sluice inlet valve is closed, (b). adjusting sluice chamber pressure to a loading pressure that is substantially atmospheric or intermediate between atmospheric and reactor pressure (c). opening the sluice inlet valve (d). force-loading a quantity of biomass into the sluice chamber at loading pressure, (e). closing the sluice inlet valve (f). adjusting sluice chamber pressure to an unloading pressure that is substantially reactor pressure or a pressure intermediate between atmospheric and reactor pressure (g). force-unloading biomass from the upper, vertical segment of the sluice chamber into a lower segment of the sluice chamber that is in communication with a vertical reactor inlet, optionally achieving compression of biomass while the sluice outlet valve is closed (h). opening the sluice outlet valve, and (i). force-unloading biomass into the vertical reactor inlet while the sluice chamber is equilibrated to unloading pressure.

In some modes of operation, some quantity of compressed biomass can be loaded into the sluice chamber with each cycle of inlet valve opening while some quantity remains in the loading chamber. This remaining material forms a partial "plug" that, when compressed to within the range of about 200-400 kg/m$^3$, and having a volume of at least about 0.1 m$^3$, can maintain a pressure seal for the duration of one cycle of inlet valve opening up to a difference pressure of about 3 bar.

The term "one cycle of inlet valve opening" refers to the time required for inlet valve opening, force-loading of a portion of biomass into the sluice chamber, and inlet valve closing. In the embodiment shown in FIG. 2, one cycle of inlet valve opening is typically between about 10 and 16 seconds. The quantity of biomass that can be loaded in one cycle of inlet valve opening is between about 75 and 150 kg dry matter. Other embodiments can readily be conceived which can handle larger quantities of biomass.

In providing a partial pressure seal, the partial "plug" permits a hybrid plug/sluice mode of operation. This is advantageous because, in this mode, the sluice chamber can be loaded at a loading pressure that is intermediate between reactor and atmospheric pressure. This reduces pump cycle time, since the sluice chamber may be loaded at a pressure that is not fully depressurized to atmospheric pressure. In the embodiment shown in FIG. 2, operating at 15 bar reactor pressure, of the time required to depressurize from 15 to 0.3 bar difference pressure, about 30% is typically required to depressurize from 3 to 0.3 bar. Thus, loading at 3 bar difference pressure significantly reduces cycle time. Reduced pump cycle time accordingly increases throughput capacity of the device.

The term "pump cycle" refers to the overall process of inlet valve opening, biomass force-loading, inlet valve closing, loading chamber re-loading, unloading segment loading, sluice pressurization to unloading pressure, outlet valve opening, biomass force-unloading, outlet valve closing, and sluice depressurization to loading pressure. Some of the functions can be arranged concurrently to optimize pump cycle time.

In the hybrid plug/sluice mode of operation, between each cycle of inlet valve opening, fresh biomass is loaded in the loading chamber behind the partial "plug" that is left remaining from the previous cycle.

A similar partial "plug" may be left remaining in the unloading segment of the sluice chamber with each cycle of outlet valve opening. This material similarly forms a partial "plug" that, when compressed to within the range of about 200-400 kg/m³, and having a volume of at least about 0.1 m³, can maintain a pressure seal for the duration of one cycle of outlet valve opening up to a pressure difference of about 3 bar between reactor pressure and sluice unloading pressure. In the embodiment shown in FIG. 2, operating at 15 bar reactor pressure, of the time required to pressurize the sluice chamber from 0.3 bar to 15 bar difference pressure, about 50% is typically required to pressurize from 12 to 15 bar. Thus, unloading at 3 bar difference pressure (e.g., 12 bar) significantly reduces cycle time and increased throughput capacity of the device.

Devices of the invention can also be effectively and efficiently used in standard sluice modes of operation where the loading chamber and unloading segment are fully emptied on each cycle of inlet and outlet valve opening. However, in these modes, the sluice chamber is generally adjusted to a loading pressure that is substantially atmospheric, about 0.3 bar or less above atmospheric pressure, and an unloading pressure that is substantially reactor pressure, about 0.3 bar or less difference pressure.

Devices of the invention can be used to load against reactors having any pressures, for example, from 5 to 40 bar, and higher. In hybrid plug/sluice modes of operation, a suitable intermediate loading pressure is typically within the range of about 0.3 to 3 bar above atmospheric, while a suitable unloading pressure is typically within the range of about 3 to 0.3 bar difference pressure.

Figure 7A:
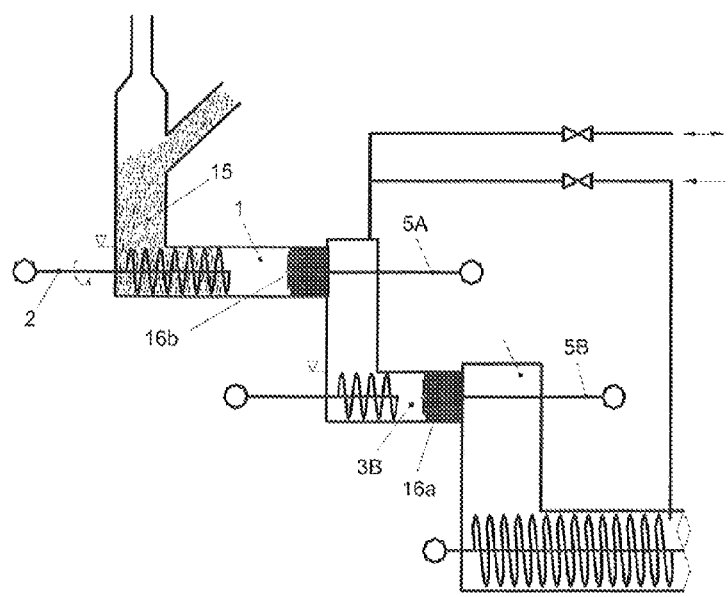
FIGS. 7A, 7B, and 7C show a schematic illustration of a hybrid plug/sluice mode of operation of the embodiment shown in FIG. 2.
Figure 7B:
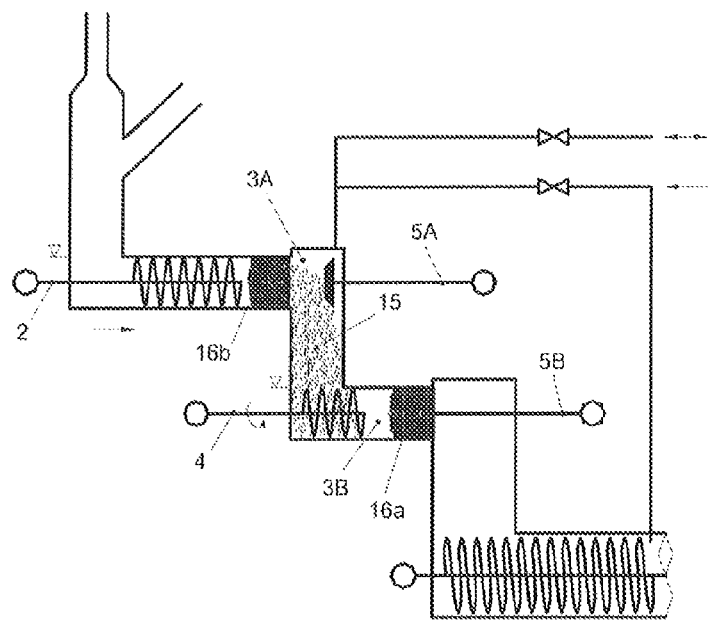
Figure 7C:
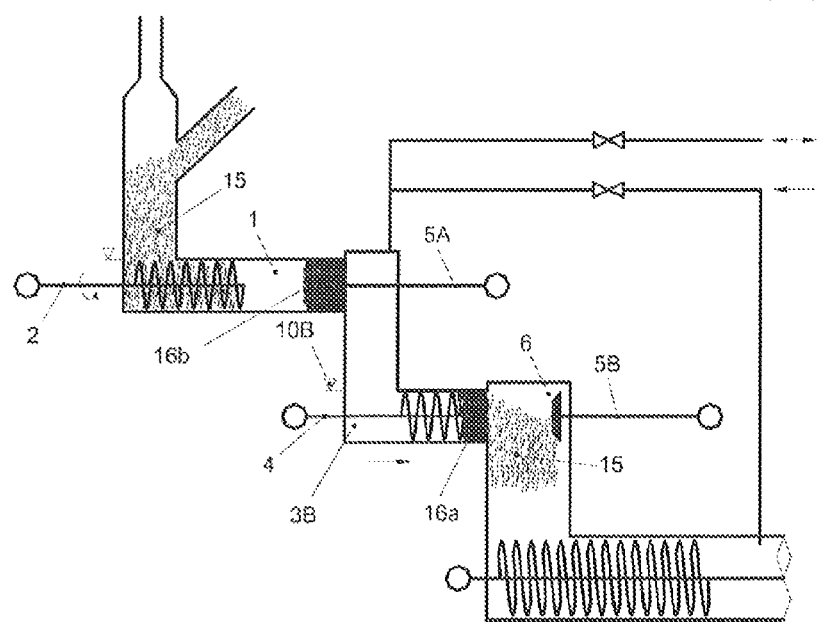

FIGS. 7A, 7B, and 7C show a schematic illustration of a hybrid plug/sluice mode of operation. As shown in FIG. 7A, at the beginning of the pump cycle in a hybrid plug/sluice mode of operation, partial plugs (16a,b) remain in both the loading chamber (1) and in the unloading segment of the sluice chamber (3B). Biomass (15) is force-loaded by screw action of the loading device (2) into the loading chamber behind the partial plug (16b) while both sluice inlet valve (5A) and sluice outlet valve (5B) are closed.

As shown in FIG. 7B, in the loading cycle, the sluice inlet valve (5A) is open, the sluice outlet valve (5B) is closed, and pressure in the sluice chamber (3A, 3B) has been adjusted to a loading pressure of about 3 bar above atmospheric. A short term seal was provided by the partial plug remaining in the loading chamber from the previous loading cycle, in combination with the loaded biomass itself. Biomass (15) is force-loaded into the vertical component of the sluice chamber (3A) by piston displacement of the loading device (2) and further compressed by screw action of the unloading device (4) into the unloading segment of the sluice chamber (3B) behind the partial plug (16a) remaining from the previous unloading cycle. A partial plug (16b) is left remaining in the loading chamber for the next loading cycle.

As shown in FIG. 7C, in the unloading cycle, the sluice outlet valve (5B) is open, the sluice inlet valve (5A) is closed, and pressure in the sluice chamber (3A, 3B) has been adjusted to an unloading pressure about 3 bar lower than reactor pressure. A short term seal was provided by the partial plug remaining from the previous unloading cycle, in combination with the unloaded biomass itself. Biomass (15) is force unloaded into the reactor inlet (6) by piston displacement of the unloading device (4). A partial plug (16a) is left remaining in the unloading segment (3B) for the next unloading cycle. Concurrently, biomass (15) is force-loaded by screw action of the loading device (2) into the loading chamber (1) behind the partial plug (16b) left remaining from the previous loading cycle.

The description of preferred embodiments is representative only and not intended to limit the scope of the invention as defined by the claims.

The invention claimed is:

1. An apparatus for removing pretreated biomass from a pressurized hydrothermal reactor comprising
    (a). A sluice chamber loading device
    (b). A sluice chamber
    (c). A sluice chamber inlet valve adapted to seal an opening to reactor pressure when closed
    (d). A sluice chamber outlet valve adapted to seal an opening to atmospheric or outlet pressure when closed and adapted for non-explosive release of pretreated biomass
    (e). A sluice chamber unloading device, and
    (f). A biomass outlet adapted for non-explosive release of pretreated biomass, and
    (g). Separate ventilation valve systems that ventilate steam from reactor pressures down to intermediate levels of pressures and from intermediate levels of pressure down to outlet pressures; wherein said sluice chamber is L-shaped.

2. The apparatus of claim 1 wherein the separate ventilation valve systems ventilate in two pressure stages.

3. The apparatus of claim 2 wherein one stage ventilates from 15 bar to 3 and one stage ventilates from 3 bar to atmospheric pressure.

4. The apparatus of claim 1 wherein the separate ventilation valve systems ventilate in three or more stages.

5. The apparatus of claim 1 further comprising an outlet chamber that is adapted to provide variable temperature and pressure conditions.

6. The apparatus of claim 5 wherein the outlet chamber is adapted to provide temperature of at least 140° C.

7. A method for removing pretreated biomass from pressurized hydrothermal reactors comprising
    (a). Providing a reactor unloading device comprising a sluice chamber that is fitted with ventilation valves that can be regulated so as to release reactor steam and thereby depressurize said sluice chamber in a process that is comparatively gradual relative to steam explosion and that further comprises a sluice chamber loading device and a sluice chamber unloading device,
    (b). Using said reactor unloading device to load pretreated biomass from a pressurized reactor into the sluice chamber through an open inlet valve that is adapted to seal an opening to reactor pressure when closed, while the outlet valve that is adapted to seal an opening to atmospheric or outlet pressure when closed,
    (c). Closing the inlet valve,
    (d). Depressurizing the sluice chamber to atmospheric or outlet pressure,
    (e). Opening the outlet valve,
    (f). Unloading the pretreated biomass at atmospheric or outlet pressure,
    (g). Closing the outlet valve, and
    (h). Repressurizing the sluice chamber prior to opening the inlet valve for an additional removal cycle.

8. The method of claim 7 wherein furfural content of the insoluble fiber fraction of unloaded biomass is less than about 50% of the furfural content within the reactor.

9. The method of claim 7 wherein depressurization is accomplished by means of separate ventilation valve systems that ventilate steam from reactor pressures down to intermediate levels of pressures and from intermediate levels of pressure down to outlet pressures.

10. The method of claim 9 wherein the separate ventilation valve systems comprise two stages.

11. The method of claim 9 wherein the separate ventilation valve systems comprise three or more stages.

12. The method of claim 7 wherein steam ventilated during depressurization is recycled to use in further production processes such as drying systems, evaporation systems, or biomass preheating.

13. The method of claim 7 further comprising subjecting biomass to further adjustments of temperature and pressure in an outlet chamber.

14. The method of claim 13 wherein the pressure in the outlet chamber is adjusted within the range 50 to 200 torr.

15. The method of claim 13 wherein the pressure in the outlet chamber is adjusted within the range 200 to 700 torr.

16. The method of claim 13 wherein the temperature in the outlet chamber is adjusted to at least 13° C.

* * * * *